United States Patent
Alfano et al.

(10) Patent No.: US 10,362,983 B2
(45) Date of Patent: Jul. 30, 2019

(54) NEAR INFRARED PHOTONIC PROSTATOSCOPY ANALYZER

(71) Applicants: Robert R. Alfano, Bronx, NY (US); Wubao Wang, Flushing, NY (US); Yang Pu, Flushing, NY (US); Yury Budansky, Oakland, NJ (US); Laura Sordillo, New York, NY (US); Guichen Tang, Flushing, NY (US); James Eastham, Tarrytown, NY (US)

(72) Inventors: Robert R. Alfano, Bronx, NY (US); Wubao Wang, Flushing, NY (US); Yang Pu, Flushing, NY (US); Yury Budansky, Oakland, NJ (US); Laura Sordillo, New York, NY (US); Guichen Tang, Flushing, NY (US); James Eastham, Tarrytown, NY (US)

(*) Notice: Subject to any disclaimer, the term of this patent is extended or adjusted under 35 U.S.C. 154(b) by 161 days.

(21) Appl. No.: 14/710,222

(22) Filed: May 12, 2015

(65) Prior Publication Data
US 2015/0320319 A1 Nov. 12, 2015

Related U.S. Application Data

(60) Provisional application No. 61/996,604, filed on May 12, 2014.

(51) Int. Cl.
*A61B 1/00* (2006.01)
*A61B 1/31* (2006.01)
*A61B 5/00* (2006.01)

(52) U.S. Cl.
CPC ........ *A61B 5/4381* (2013.01); *A61B 1/00142* (2013.01); *A61B 1/00165* (2013.01);
(Continued)

(58) Field of Classification Search
CPC .................................. A61B 5/00; A61B 1/00
See application file for complete search history.

(56) References Cited

U.S. PATENT DOCUMENTS

| | | | | |
|---|---|---|---|---|
| 5,795,632 A | * | 8/1998 | Buchalter | A61B 8/12 206/305 |
| 6,037,770 A | * | 3/2000 | Itoh | G01R 33/0322 324/244.1 |

(Continued)

OTHER PUBLICATIONS

Pu, Y., et al. "Near infrared photonic finger imager for prostate cancer screening." Technology in cancer research & treatment 10.6 (2011): 507-517.*

(Continued)

*Primary Examiner* — Luther Behringer
*Assistant Examiner* — Sean D Mattson
(74) *Attorney, Agent, or Firm* — Myron Greenspan; Lackenbach Siegel LLP

(57) ABSTRACT

A rectal near infrared (NIR) scanning polarization imaging system uses NIR Photonic Prostatoscopy Analyzer (NIR-PPA) for prostate cancer detection using light. The NIRPPA consists of a portable rectal NIR scanning polarization imaging unit and an optical fiber-based rectal probe capable of recording sets of 2D images of a prostate through rectum at different wavelengths and depths and obtaining a three dimensional (3D) image of the prostate and 3D locations of abnormal tissue inside the prostate. Diode lasers/light emission diodes (LEDs) with selected emitting wavelengths are used in the NIR spectral range from 650 nm to 2,400 nm corresponding to the four tissue optical windows (#I, 650 nm-950 nm; #II, 1,100 nm-1,350 nm; #III, 1,600 nm-1,870 nm; and #IV, 2,100 nm-2,300 nm). The fingerprint absorptions of water ($H_2O$), Oxyhemoglobin ($HbO_2$) and deoxyhemoglobin (Hb) in the prostate are used as native biomarkers for prostate cancer detection.

17 Claims, 11 Drawing Sheets

(52) U.S. Cl.
CPC ............ *A61B 1/00172* (2013.01); *A61B 1/31* (2013.01); *A61B 5/0062* (2013.01); *A61B 5/0066* (2013.01); *A61B 5/0086* (2013.01)

(56) References Cited

U.S. PATENT DOCUMENTS

| | | | |
|---|---|---|---|
| 7,706,862 | B2 | 4/2010 | Alfano et al. |
| 7,826,878 | B2 | 11/2010 | Alfano et al. |
| 2003/0171678 | A1* | 9/2003 | Batten ............... A61B 8/0833 600/443 |
| 2003/0232445 | A1* | 12/2003 | Fulghum, Jr. ........ A61B 5/0071 436/63 |
| 2005/0270539 | A1* | 12/2005 | Abbink ............... G01J 3/453 356/451 |
| 2006/0173355 | A1* | 8/2006 | Alfano ............... A61B 5/0059 600/476 |
| 2009/0323076 | A1* | 12/2009 | Li ...................... A61B 5/0066 356/479 |
| 2012/0075619 | A1* | 3/2012 | Nieman ............... G01B 11/22 356/72 |
| 2013/0296708 | A1* | 11/2013 | Zuzak ................. A61B 5/0071 600/476 |

OTHER PUBLICATIONS

Laura A. Sordillo, Yang Pu, Sebastiao Pratavieira, Yury Budansky, and Robert R. Alfano, "Deep optical imaging of tissue using the second and third near-infrared spectral windows", submitted to Journal of Biomedical Optics for publication.

Y. Pu, W.B. Wang, M. Xu, G.C. Tang, Y. Budansky, M Sharanov, S. Achilefu, J.A. Eastham and R. R. Alfano, "Near infrared photonic finger imager for prostate cancer screening", Technol. Cancer Res. Treat, (Technology of Cancer Research and Treatment), 10, Issue 6, 507-517 (2011).

M. Xu, M. Alrubaiee, S K. Gayen and R. R Alfano (2005). "Three-dimensional localization and optical imaging of objects in turbid media using independent component analysis," Appl. Opt.44: 1889-1897, 2005.

Ferrini, R., and Woolf, S. H., "Screening for Prostate Cancer in American Men", http://www.acpm.org/prostate.htm, American College of Preventive Medicine—Practice Policy Statement.

Gleason, D. F., (1977), "The Veteran's Administration Cooperative Urologic Research Group: histologic grading and clinical staging of prostatic carcinoma", In Tannenbaum, M. Urologic Pathology: The Prostate, Philadelphia: Lea and Febiger, pp. 171-198. ISBN 0-8121-0546-X.

Epstein, J. I., Allsbrook, W. C. Jr, Amin, M. B., and Egevad, L. L.: ISUP Grading Committee, (2005), The 2005 International Society of Urological Pathology (ISUP) Consensus Conference on Gleason Grading of Prostatic Carcinoma, Am. J. Surg. Pathol; 29(9), 1228-42.

* cited by examiner

Fig. 6(a) Fig. 6(b)
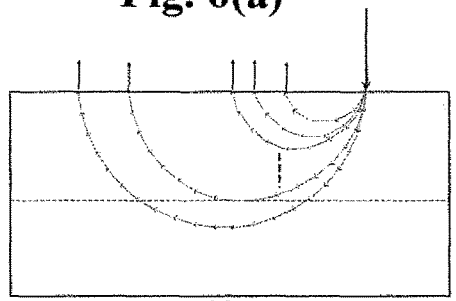
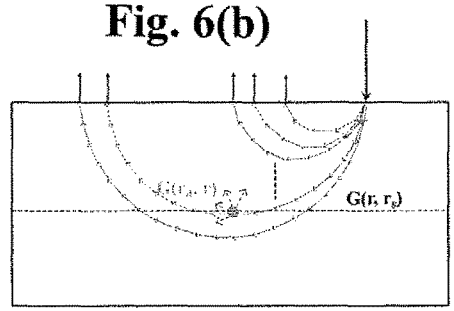
(a) no object
(b) single object
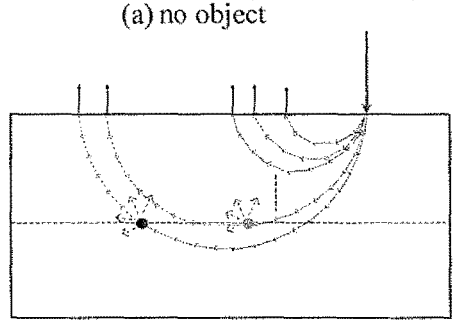
(c) multiple object
(d) scanning incident beam
Fig. 6(c) Fig. 6(d)

NEAR INFRARED PHOTONIC PROSTATOSCOPY ANALYZER

BACKGROUND OF THE INVENTION

1. Field of the Invention

The invention generally relates to systems and methods of detecting cancer and, more specifically to an near infrared photonic prostatoscopy analyzer.

2. Description of Prior Art

The common screening tests for prostate cancer diagnosis are digital rectal examination (DRE), prostate specific antigen (PSA) blood test, and the transrectal ultrasound (TRUS) imaging. A value of PSA over 4.0 ng/ml is the commonly used threshold for further diagnostic evaluation. Although PSA test appears to have acceptable sensitivity for late stage cancer and disease with histopathologic features associated with tumor progression of a large volume, poorly differentiated cells and extracapsular penetration, its accuracy is limited as low as 28%-35%. During the DRE, a doctor inserts a lubricated gloved finger into the patient's rectum to feel for the enlargements and hard areas of prostate that might indicate prostate cancer. DRE has a reported sensitivity of 18%-22%. TRUS is no longer considered as a first-line screening test for prostate cancer because of its poor spatial resolution and contrast, but it does play a role in mapping the locations of the biopsy sampling. The confirmation of prostate cancer finally needs a needle biopsy of the prostate. In the biopsy, a number (12-18) of cores of prostate tissue are randomly taken from whole region of the prostate using a thin needle with the help of TRUS to map the locations of the sampling.

The early detection and treatment of prostate cancers can significantly reduce mortality. Conventional oncology imaging methods for prostate cancer diagnosis still depend on bulk physical properties of cancer tissue and are not effective for early-stage primary tumors. Since PSA and DRE have limited accuracy, TRUS has poor contrast between normal and abnormal tissue regions, and needle biopsy is invasive and may cause damage to the prostate, it is highly desirable to develop a better method which is accurate, of higher spatial resolution, and non-or-less invasive for prostate cancer screening.

Optical imaging technique using near infrared (NIR) light from 650 nm to 2,400 nm in the four tissue optical windows (Window #I, 650 nm-950 nm; Window #II, 1,100 nm-1,350 nm; Window #III, 1,600 nm-1,870 nm; and Window #IV, 2,100 nm-2,300 nm) as shown in FIG. 4 provides an attractive noninvasive approach for screening human diseases [1]. These four "tissue optical windows" in the NIR range, which correspond to lower absorption of major tissue chromophores such as water, oxygenated and deoxygenated hemoglobin, allow light to penetrate deeply into the tissue up to several centimeters. As indicated in FIG. 4, the tissue scattering is much less in windows #II-#IV reducing image blurring. The other main advantages of the NIR optical approaches are its low-cost, the ability to monitor multiple independent optical reporters simultaneously in vivo using light with different wavelengths, the absence of radioactive intermediates, and the relative simplicity of the imaging hardware as compared with. Magnetic Resonance Imaging (MRI) and Positron Emission Tomography (PET) equipment. These advantages make optical imaging unmatched by any other in vivo imaging techniques. The major disadvantage of the optical imaging approaches is that high scattering of biological tissue causes most photons to diffuse. A very small percentage of ballistic and snake photons makes direct imaging practically only in surface layers of tissue. Scientists have to use the four NIR tissue windows for deep imaging and reducing the image blurring, and explore optical tomography methods and/or inverse image reconstruction approaches to obtain 3D images of target organs and locate the three dimension (3D) positions of the abnormal tissue and recover the 3D spatial distribution information of optical parameters of the whole tissue. When light transports in a highly scattering medium such as tissue, the blurred transmission or backscattered images are rendered to us. The behavior of diffusion essentially depends on optical properties of the tissue medium such as scattering coefficient ($\mu_s$), anisotropy factor (g) and absorption coefficient ($\mu_a$). Since the transmittance and backscattered images are acquired from those photons surviving passage from the tissue, which may contain clues about their voyage and the optical coefficients of the tissue, the measured light intensity distribution on the boundary of the turbid medium can be used to generate a map of the $\mu_s$ and $\mu_a$ of the whole tissue medium using an inversion algorithm.

To reduce image blurring and improve image quality, the four NIR tissue windows from 650 nm to 2,400 nm can be used. The CCD/CMOS cameras used to detect light in these four NIR windows can be Si-based (response for the spectral range of 400 nm-1,000 nm), InGaAs-based (1,000 nm-1,800 nm) and InSb-based (1,000 nm-5,000 nm) cameras. The tissue scattering is less for the longer NIR wavelengths as the scattering cross section ($\sigma_s$) is proportional to $1/\lambda^n$, where n>1 for $\lambda$>400 nm. FIG. 4(a) shows the spectra of the total attenuation coefficient ($\mu_t$) from the normal prostate tissue using the #I, #II, #III and #IV NIR windows, and FIG. 4(b) shows the spectra of the total attenuation length ($l_t$) in μm from normal and cancerous prostate tissues using the #I, #II, #III, and #IV NIR tissue optical windows, where $l_t$ is inversely proportional to $\mu_t$.

The important absorption biochemical components (chromophores) in tissue that can be detected in the absorption measurements are water ($H_2O$), oxyhemoglobin ($HbO_2$) and deoxyhemoglobin (Hb). Since cancerous and normal prostate tissues have different water contents due to the development of cancer, the change of absorption and relative contents of $H_2O$ can be used as a potential fingerprint of native biomarkers to distinguish cancerous and normal prostate tissues [1]. Other critical native biomarkers are $HbO_2$ and Hb, and changes of their relative contents are also sensitive to the cancer evolution. As a tumor grows, it rapidly outgrows its blood supply, leaving portions of the tumor with regions where the oxygen concentration is significantly lower than in healthy tissue regions. The change of the relative contents of $HbO_2$ and Hb is usually measured using an oxygen saturation factor, which is defined as $SO_2 = C_{HbO2}/(C_{HbO2} + C_{Hb})$, where the $C_{HbO2}$ and $C_{Hb}$ are molar concentrations of $HbO_2$ and Hb in tissue, respectively. The lower value of $SO_2$ in a tissue area may indicate the existence of tumor in the area. Tumor hypoxia is the situation where tumor cells have been deprived of oxygen, and may be used to help diagnosis of tumors/cancers. As a result, change of water contents and values of $SO_2$ (hypoxia) in prostate tissue areas obtained from the absorption and/or imaging measurements can be used as potential fingerprints of native biomarkers to evaluate existence and obtain 3D location of cancer areas.

To obtain a 3D image and locate the 3D position of cancerous prostate tissue embedded in normal prostate tissue, a portable rectal NIR scanning polarization imaging unit with an optical fiber-based rectal probe was developed and tested using NIR light ranged from 650 nm to 2400 nm.

This transrectal scanning polarization imaging system was used to obtain 3D images and locate the 3D positions of abnormal prostate tissue hidden in normal prostate tissue based on differences of optical parameters between cancerous and normal prostate tissues. The scanning polarization imaging system can be used to acquire a set of 2D images by sequentially scanning a polarized illuminating light beam at different areas of a prostate gland through rectum, and obtain the distribution of light intensity backscattered from the prostate using a CCD/CMOS camera. An Independent Component Analysis (ICA)-based inverse image reconstruction algorithm was improved specifically for the application of backscattering configuration and used to obtain 3D images and locate the 3D positions of foreign inhomogeneities from the recorded array of the 2D images. Therefore, NIRPPA may introduce a new criteria/indicator for prostate cancer screening in addition to the conventional examinations to enhance the accuracy of prostate cancer detection.

SUMMARY OF THE INVENTION

The present invention provides a novel NIRPPA system for diagnostic function as a screening tool other than DRE, PSA and TRUS based on different absorption and scattering properties of light backscattered from cancerous and normal prostate tissues using native biomarkers of $H_2O$, $HbO_2$, and Hb in the four NIR tissue optical windows. The system provided by the present invention can overcome at least some of the problems associated with conventional screening techniques mentioned above. In particular, the present invention provides an optical system to detect 3D images and localize the 3D positions of abnormal prostate tissue hidden inside the normal prostate tissue through the human rectum in near-real-time. The present invention can also provide a system that has extended wide applications for the near real-time detection and 3D imaging and localization of tumor inside other organs such as rectum, colon, bladder, oral cavity and esophagus.

The present invention discloses a novel NIRPPA system for detection of 3D images and 3D position determination of prostate cancer, and its applications for detection of cancers in rectum, colon, bladder, oral cavity and esophagus. The disclosed system employs an illuminating light beam output from laser diodes/light emission diodes (LEDs) with selective NIR wavelengths, optical components (band pass filters, polarizers, and lenses), illumination and imaging coherent optical fiber-bundles, optical fiber-based rectal probe, optical detectors (CCD/CMOS cameras with USB interface), miniature scanning Galvanometric mirrors with their electronic control boards (servo driver circuit boards) and the corresponding self-developed LabVIEW software.

A photograph and a schematic diagram of the NIRPPA system, a portable rectal NIR scanning polarization imaging unit with a optical rectal probe, are shown in FIGS. 1(a) and 1(b), respectively. As examples, three laser diodes emitting in the Window #I region at 650 nm, 750 nm and 980 nm are alternatively used as light sources. These wavelengths were selected to probe the native molecules such as $H_2O$, Hb and $HbO_2$ in tissues. Water content and value of hypoxia are used as fingerprints for cancer detection. For NIR tissue windows #II, #III and #IV, laser diodes/LEDs emitted at longer wavelengths in the spectral ranges of 1,100 nm-1,350 nm, 1,600 nm-1,870 nm, and 2,100 nm-2,300 nm can be used, respectively, as light sources. The output beam from a laser diode is directed to the scanning galvanometric mirror system after passing through two pinholes. The beam can be scanned by two miniature galvanometric mirrors in the x- and y-directions, respectively. The beam output from the galvanometric mirrors is focused using a microscopy objective lens into a coherent fiber-bundle used for illumination. The position of the microscopy objective lens can be adjusted in the x-, y- and z-three directions for the beam-fiber coupling. The output beam from the illumination fiber is directed to a small reflection prism located inside the rectal probe after passing through a polarizer (P1), which is located in the output side of the illumination fiber-bundle and used to ensure that the illumination beam is linearly (or other type-) polarized. The beam reflected from the prism is used to illuminate a prostate gland through rectum. This illumination beam with a diameter of ~1 mm can be scanned in the x- and y-directions on the prostate.

The light backscattered (or emitted) from a prostate sample first passes through the rectal wall and reflected from the prism inside the probe head. The beam is then collected by a lens into another coherent fiber-bundle used for imaging after passing through another polarizer (P2) functioning as an analyzer to obtain images with different polarization configurations relative to $P_1$. The image information formed in the optical fiber bundle is sent to a CCD/CMOS camera through the coherent imaging fiber bundle and coupling lens for recording 2D images of the prostate sample. For the NIR tissue window #I, a Si-based CCD camera responding for the spectral range of 400 nm-1,000 nm is used. For tissue NIR windows #II, #III, and #IV, the InGaAs-based (for 1,000 nm-1,800 nm) and InSb-based CCD/CMOS (for 1,000 nm-5,000 nm) cameras can be used to detect the NIR light backscattered or emitted from the prostate. A band pass filter is placed in front of the CCD/CMOS camera to record the 2D images at different wavelengths. A cross-polarization image for each scanned illumination position of the laser beam is recorded when the polarization direction of $P_2$ is perpendicular to that of $P_1$ to suppress the contribution of light scattered (or emitted) from the surface and sub-surfaces to the images of the prostate sample. When the illumination light beam is scanned in the x-y plane of the sample with n×n points, an array of $n^2$ 2D images will be recorded. The key part of the scanning imaging unit is the scan of the illumination beam on the surface of the prostate sample with adjustable scanning parameters such as scanning area, step, speed and the number of scanning points.

FIG. 1(b) schematically shows the layout of the major parts and the control boards for the NIRPPA system, which consists of (1) the Dual Axis galvanometric mirrors GV1, GV2, (2) the two servo driver circuit boards and their power supply, (3) the drive unit for sending voltage output to servo circuit boards, and (4) a personal computer (PC) with an installed LabVIEW software to power and send a command to DAQ USB 9263 to generate desired output voltage through a USB connection. In the scanning system, the drive unit NI-9263 powered by USB interface of the PC, is used to generate an analog voltage, which can be varied from −10 V to +10 V using the LabVIEW software. This analog voltage is sent to the two servo driver boards to drive the rotations of the Galvo Mirrors. For example, 1V input to the servo board can make the mirror rotate 1°. One servo board controls the X-axis, and another is for Y-axis. Both servo driver boards are powered by the power supply of GPS011. The beam scanning, the image acquiring and recording, and the synchronization of scanning and imaging processes are controlled by the Graphical User Interface (GUI) software developed using LabVIEW. All parameters of the scanning imaging system (the position of the original, scanning steps, step size, exposure time, and waiting time between two adjacent images acquiring) can be adjusted through the GUI.

In order to study tissue scattering and imaging properties in the four NIR windows, optical attenuation measurements for thin tissue slices of normal and malignant breast and prostate tissue, pig brain and chicken tissue were performed in the spectral range from 400 nm to 2,500 nm. [1] Optical images of model chicken tissue samples were also obtained using the second and third spectral windows. Due to a reduction in scattering and minimal absorption, the longer attenuation and clearer images could be seen in the second and third NIR windows compared to the conventional first NIR window. A possible fourth optical window centered at 2,200 nm was noted. As parts of results, FIG. 4(a) shows the spectrum of the total attenuation coefficient ($\mu_t$) from the normal prostate tissue using #I, #II, #III and #IV NIR windows, and FIG. 4(b) shows the spectra of the total attenuation length ($l_t$) in μm from normal and cancerous prostate tissues in #I, #II, #III, and #IV NIR tissue optical windows, where the total attenuation lengths ($l_t$) is inversely proportional to the total attenuation coefficient ($\mu_t$). The results indicate that longer attenuation lengths can be seen in the second and third NIR windows, and may provide additional information to that observed using the conventional first NIR window. It can also be seen that $l_t$ from normal prostate tissue is larger compared to the malignant tissue samples.

The present invention is based on specific design and arrangement of scanning light sources, coherence fibers for excitation and imaging, and an optical rectal probe with specific size to acquire a set of 2D images. As presented in our previous patent [2], there is a difference of water absorption between cancerous and normal prostate tissues, which can be used to image the difference of cancerous and normal prostate tissues with a large beam without scanning. However, without beam scanning, one can only detect cancerous tissue in two dimensions (2D) with a limited resolution. In the present invention, a scanning polarization imaging system is used to measure light intensity distributions caused by scattering and/or emission of cancerous and normal prostate tissues at the critical wavelength(s). By this way, the scanning optical imaging system can be used to acquire the multiple optical signals with multiple illumination (using scanning) and multiple detection (using CCD/CMOS cameras), which can be used for blind source analysis to identify and obtain the 3D images and positions of abnormal tissues with a higher resolution. In particular, the depth of cancerous tissue hidden inside the normal tissue can be obtained. In addition, this system, which applies the probe with a proper size, can be used to image the prostate through rectum to achieve the in vivo screening study.

The present invention is also based on our recent studies of cancerous prostate tissue embedded in normal prostate tissue samples using the NIRPPA system with the inverse image reconstruction algorithms, namely Optical Tomography using Independent Component Analysis (OPTICA) introduced in our previous patent for the forward scattering configuration [3]. The disclosures, including the algorithms, in U.S. Pat. No. 7,706,862 is incorporated by reference as if fully set forth herein. In the present invention study of 3D images and localizations of objects in biological tissue using independent component analysis (ICA) in reflection (backscattering) geometry which is suitable for prostate cancer detection, the light backscattered from a sample in response to a scanning laser beam recorded by a CCD/CMOS camera is used to obtain multiple angular views of the objects embedded inside the tissue medium. The retrieved independent component corresponds to the projection of the Green's function of light propagating from the object to the boundary of the tissue medium. The difficulty arises in reflection geometry because the incident beam profile and the surface property of the sample affect appreciably the spatial distribution of the backscattered light. Such issues are not as important in transmission geometry. We address this challenge problem by numerically marching the target to the surface until matching the retrieved independent component, incorporating both the beam profile and the surface property of the sample. The 3D image and 3D location fitting model and software have been developed accordingly based on the approach of numerical marching.

Scanning imaging experiments were performed on model prostate tissue samples in the NIR window #I region to distinguish in vitro cancerous prostate tissue from surrounding normal prostate tissue using the NIRPPA system. The sample consists of a small piece of cancerous prostate tissue embedded inside a large piece of normal prostate tissue at the depth of z=3.0 mm from the front surface. The thickness of the whole tissue sample is 10 mm. As shown in FIG. 10, after the OPTICA analysis, the independent intensity distribution attributed from the cancerous prostate tissue embedded in normal tissue can be extracted using the improved OPTICA for backscattering configuration [3]. FIGS. 10(a) and 10(c) are for the leading independent component, and FIGS. 10(b) and 10(d) are for the residual (noise) component. It is clear that the existence of target (the cancerous prostate tissue) can be realized from FIGS. 10(a) and 10(c). The x- and y-locations of the cancer tissue can be obtained from FIG. 10(c). The z-location of the cancerous prostate tissue (leading IC) can be obtained by fitting Green's function of the target numerically marching to the surface of the medium obeying diffusion approximation which yields z=3.1 mm, that is in good agreement with the real depth of ~3 mm. In particular, a target object hidden inside the tissue media in the depth of up to ~7 times larger than the transport mean-free path of the tissue medium was identified, and the 3D locations of a small piece of cancerous prostate tissue embedded in the host normal prostate tissue were obtained from the ICA-based inverse imaging reconstruction. This demonstrates that using the NIRPPA combined with the OPTICA algorithm, one can detect and image the cancerous positions in 3D inside the prostate.

The broad impact of our work is that the approach of the numerical marching is applicable to different medium geometries, and can be used with any suitable photon propagation model. It is also amenable to near-real-time imaging applications because the current computing time for obtaining a 3D image of an inhomogeneity object in tissue media is less than 3 minutes using a Dell PC with the memory (RAM) of 4 GB and a of Pentium® processor Dual-Core CPU E5400 at 2.70 GHz, and can be improved in future.

The present invention can be extensively applied for the near real-time detection and 3D imaging of tumors inside other organs in human and animal bodies, such as rectum, colon, oral cavity and esophagus. The advantages of the systems described in the present invention are 3D imaging and location, high sensitivity and accuracy, fast (near real-time) imaging and analysis, and non invasive and safe detection.

BRIEF DESCRIPTION OF THE DRAWINGS

Those skilled in the art will appreciate the improvements and advantages that derive from the present invention upon reading the following detailed description, claims, and drawings, in which:

FIG. 6(a) shows the graphical illustration for the OPTICA algorithm: the formation of a backscattering image of homogeneous host medium without inhomogeneous object(s); FIG. 6(b) shows the formation of backscattering image of host medium with one object, which has detectable perturbation of intensity distribution from the image of the medium without object(s); FIG. 6(c) shows the formation of a backscattering image of host medium with multiple inhomogeneous objects. The image is formed by mixing diffused photons with information of multiple objects; and FIG. 6(d) shows the mechanism of multiple sources and multiple detectors by using a CCD/CMOS camera and scanning the illuminated laser source at different positions on samples, which acquires information needed for ICA.

DETAILED DESCRIPTION OF PREFERRED EMBODIMENTS

Figure 1A:
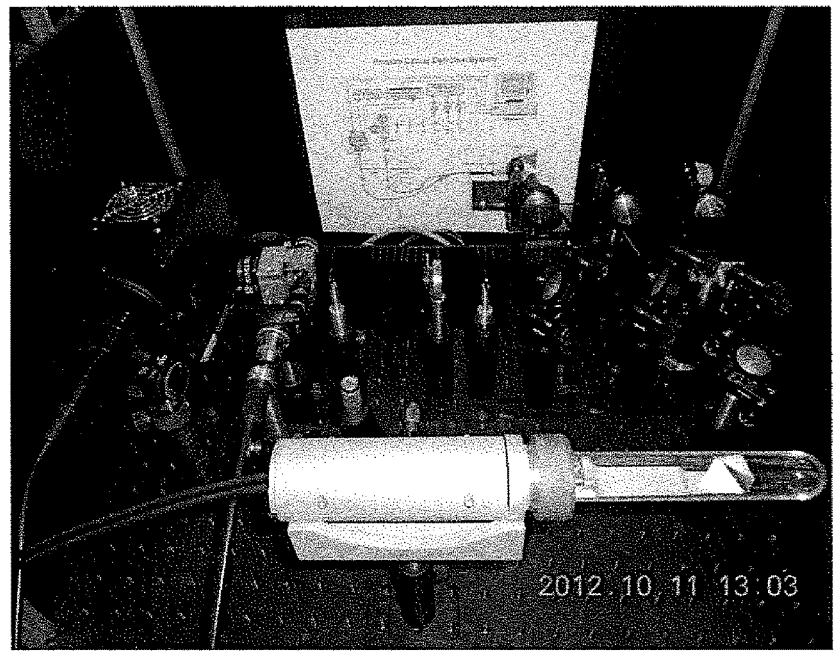
FIG. 1(a) shows a photograph and FIG. 1(b) shows a schematic diagram of the NIR Photonic Prostatoscopy Analyzer (NIRPPA) system, a portable rectal NIR scanning polarization imaging unit with an optical fiber-based rectal probe. The power supplies and computer system are not shown in the photograph. In the schematic diagram, L-laser, M-mirror, A-aperture, P-polarizer, GV-galvanometric scanning mirror, BPF-band pass filter, MOL-microscopy objective lens.

The present invention is directed to a novel NIRPPA system, which can be used for detecting cancerous tissue embedded in prostate and other deep organs using the four NIR tissue optical windows to improve livability of patients. In the application, the optical fiber-based rectal probe with a specific size can be inserted into a rectum. The illumination NIR light output from laser diodes/LEDs is directed to the scanning galvanometric mirrors. The beam output from the galvanometric mirrors is focused into a coherent optical fiber-bundle used for illumination. The output beam from the illumination fiber-bundle is first passed through a polarizer to generate linear or circular polarized illumination light, and then directed to a small reflection prism. Both of the polarizer and prism were located inside the optical rectal probe. The beam reflected from the prism is used to illuminate a prostate sample. This illumination beam can be scanned from point to point in the x- and y-directions on the surface of the prostate controlled through the Galvanometric mirrors located outside of the body. The size of the illumination beam and the imaging area, and the scan steps and speed can be varied.

The NIR light back-scattered from the prostate tissue sample first passes through the transparent tube of the probe head, and be reflected from the prism, and is then collected by a lens into another coherent fiber-bundle to form a 2D image of the prostate. Before the light is collected into this coherent imaging fiber-bundle, it passes through another linear or circular polarizer (namely analyzer) placed in front of the imaging fiber-bundle. This analyzer is kept in the polarization direction which is perpendicular (or different rotational circular polarization) to that of the illuminating light to reduce the contribution of surface scattering. The image-collecting coherent fiber-bundle is coupled with a CCD/CMOS camera to transfer images point-by-point to the camera, and record the 2D images. The band pass filters placed in front of the CCD/CMOS camera is used to pass, for the scattering light images, the scattering light at the desired wavelength and discriminate the fluorescence light emitted from prostate and rectum tissues, or to pass, for the tissue or contrast agent emission light images, the emission light and discriminate the scattering light. Typical, a total number of $n^2$ 2D images will be recorded with an illumination spot scanning by n×n at the x-y plane parallel to the surface of the prostate sample. For example, the total number of 256 2D images will be obtained with a scan of 16×16 points at the x-y plane. If the radii of the illumination beam are ~1.5 mm, the separation of two labor illumination spots is 3.0 mm, the scan of 16×16 spots will cover the area of 48 mm×48 mm for the prostate. The better spatial resolution can be obtained with a smaller illumination beam size and a larger number of scan spots.

The recorded arrays of the 2D scanning images will be used to reconstruct a 3D image of a prostate using an inverse image reconstruction algorithm and software program. The reconstructed 3D image of the prostate will be used to distinguish cancerous prostate tissue areas and detect the 3D location of the cancerous areas. The time for 2D image recording and 3D image reconstruction is fast. For example, with an image-recording rate of 8 images per second, the total time for recording 256 (16×16) images will be about 32 seconds. The estimated imaging reconstruction time for obtaining a 3D image from the recorded 256 2D images is less than 3 minutes. Since the rectal NIR scanning images have high contrast for cancerous and normal prostate tissues, a small prostate cancer, which could not be detected by other methods, may be visualized from the reconstructed 3D optical images.

Figure 1B:
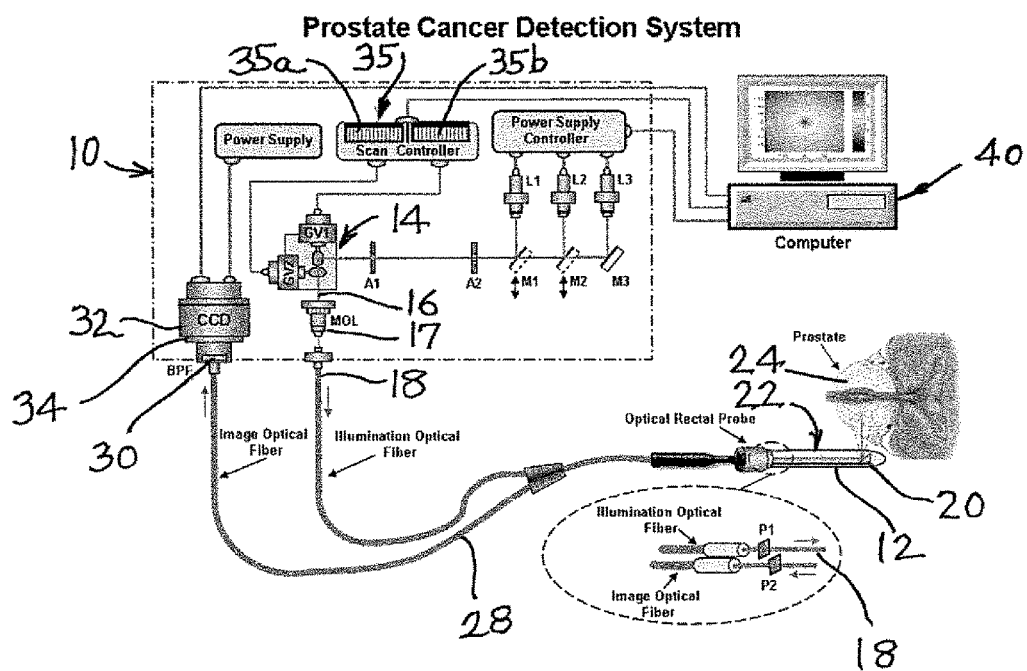

Referring to FIGS. 1($a$) and 1($b$), a photograph and schematic of the NIRPPA system consisting of a portable rectal NIR scanning polarization imaging unit 10 and an optical rectal probe 12. For NIR tissue optical window #I, three diode lasers L1, L2, L3 emitting at 650 nm, 750 nm, and 980 nm, respectively, are alternatively used as light sources. The NIR beam output from a laser diode/LED is directed into the scanning galvanometric mirror system 14 (ThorLab GVSM002 with Dual Axis Galvo Mirrors) after passing through two pinholes ($A_1$ and $A_2$). The beam can be scanned by two miniature galvanometric mirrors GV1, GV2 in the x- and y-directions, respectively. The beam output 16 from the galvanometric mirrors is focused using a microscopy objective lens 17 (MOL) into a coherent fiber-bundle 18 (Mytiad Fiber Imaging, 20-0826 Fiberscope Assay) used for illumination. The position of the microscopy objective lens (MOL) can be adjusted in the x-, y- and z-directions for the beam-fiber coupling. The output beam from the illumination fiber 18 is directed to a small reflection prism 20 located inside the rectal probe 22 after passing through a polarizer (P1), which is located in the output side of the illumination fiber-bundle and used to ensure that the illumination beam is linearly polarized. The beam reflected from the prism is used to illuminate a prostate sample 24 through rectum. This illumination beam with a diameter of ~1 mm can be scanned in the x- and y-directions on the surface of the prostate sample.

The NIR light backscattered (or emitted) from a prostate sample is first passed through the rectal wall and reflected from the prism 20 inside the probe head. The diameter of the probe tube is ~2 cm and the length is ~12 cm. The beam is then collected by a lens 26 (FIG. 2$a$) into another coherent fiber-bundle 28 (Mytiad Fiber Imaging, 20-0826 Fiberscope Assay) used for imaging after passing through another polarizer (P2) used to obtain images with different polarization configurations. The diameter of a single fiber in the bundle is ~3.2 µm with numerical aperture N.A.≅0.4. The image information formed in the optical fiber bundle is sent to a CCD/CMOS camera through the coherent imaging fiber bundle and coupling lens for recording 2D images of the prostate sample. The coupling loss of the system is ~10% and the transverse resolution is 100 µm associated with Air Force resolution target bar chart (AFBC) at group 3. A band pass filter 30 (BPF) is placed in front of the CCD/CMOS camera 32 to record the 2D images at different wavelengths. A cross-polarization image for each scanned illumination position of the laser beam is recorded when the polarization direction of P2 is perpendicular to that of P1 to suppress the contribution of light scattered (or emitted) from the surface and sub-surfaces to the images of the prostate sample. For the backscattering light imaging, a narrow band pass filter 30 corresponding to the illumination wavelength is used in front of the CCD/CMOS camera 32 to ensure that the recorded images are formed only by the light backscattered from the prostate sample. For the tissue emission and/or contrast agent emission light imaging, a long band pass filter 34 is used in front of the CCD/CMOS camera to ensure that the recorded images are formed only by the light emitted from the prostate sample. When the illumination light beam is scanned in the x-y plane of the sample with n×n points, an array of $n^2$ 2D images will be recorded.

Referring to FIG. 1($b$), a schematic diagram of the major parts and the control boards for the NIRPPA unit. This scanning system consists of (1) the Dual Axis Galvo mirrors GV1, GV2 (ThorLab GVS 002), (2) two servo driver circuit boards 35$a$, 35$b$ and their power supply (not shown) (ThorLab, GPS011) on the scan controller 35, (3) the drive unit (not shown) on the scan controller 35 for sending voltage output to servo circuit boards 35$a$, 35$b$ (National Instruments, NI DAQmx USB-9263 USB DAQ—data acquisition), and (4) a PC 40 with an installed LabVIEW software (LabVIEW Signal Express 2009) to power and send a command to DAQ USB 9263 to generate desired output voltage through a USB connection. In the scanning system, the drive unit NI-9263 powered by USB interface of the PC, is used to generate an analog voltage, which can be varied from −10 V to +10 V using the LabVIEW software. This analog voltage is sent to the two servo driver boards to drive the rotations of the Galvanometric Mirrors. For example, 1V input to the servo board can make the mirror rotate 1°. One servo board controls the X-axis, and another is for Y-axis. Both servo driver boards are powered by the power supply of GPS011.

Figure 2A:
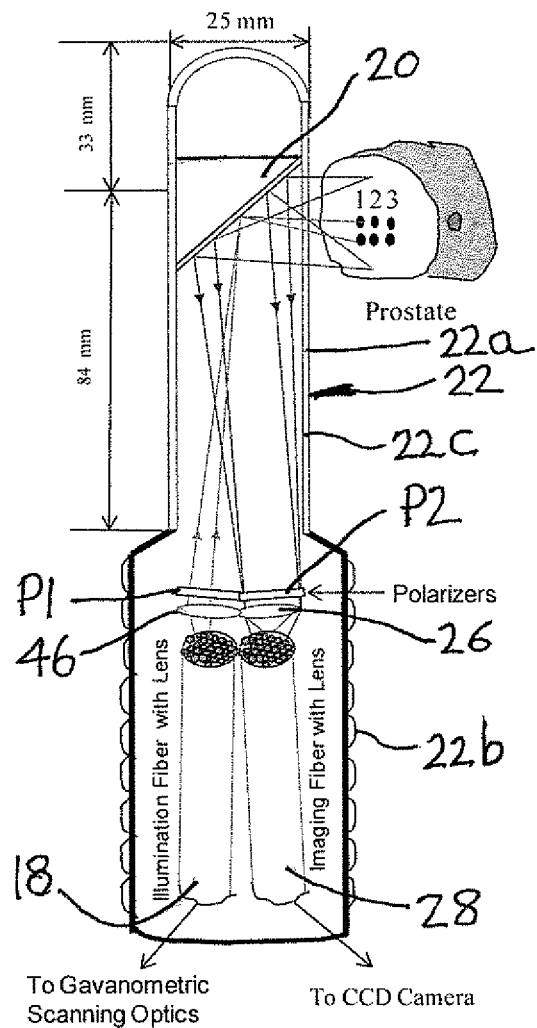
FIG. 2(a) shows a schematic diagram and FIG. 2(b) shows a photograph of the optical fiber-based rectal probe for the NIRPPA system.
Figure 2B:
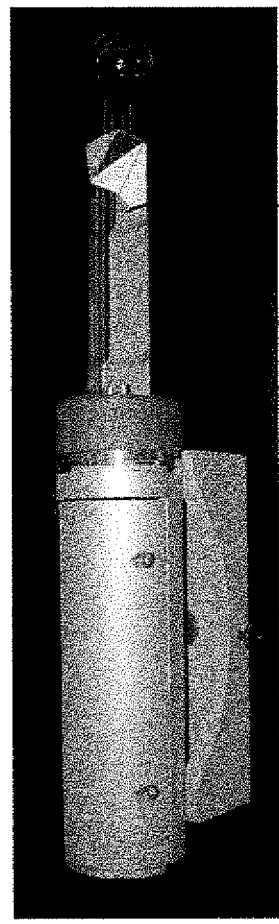

Referring to schematic diagram 2($a$) and photograph 2($b$) of the optical fiber-based rectal probe 22 of the NIRPPA system. The optical rectal probe 22 for the NIRPPA is made to be suitable and accurate for clinical applications and safer for patients to do the optical rectal scanning polarization imaging tests. The diameter and length of the probe are ~2.2 cm and ~12 cm, respectively. The major advantages of the rectal probe include: (1) using a removable transparent plastic/glass tube as a cover tube for the optical probe head instead of a fixed tube so that in clinical applications, a cover tube can be removed after finishing an optical scanning imaging measurement for one patient, and a new cover tube can be used for the next patient. The use of a disposable cover tube is safer for patients to do optical rectal imaging tests; (2) Both illumination and detection polarizers P1, P2 are placed in front of the optical fibers inside the rectal probe tube as shown in FIG. 2 instead of placing them in front of the galvanometric mirror and the CCD/CMOS camera 32 located outside the probe head to avoid the de-polarization effects in the optical fiber. Although both the illumination and imaging fibers 18, 28 are coherent, they are not polarization-preserved. If a polarizer is placed in the input path of such optical fiber, the beam output from the fiber will not be completely polarized. With the current locations and configurations of polarizers, the polarized scanning images can be accurately obtained with the desired polarization directions, and the 3D images and locations of the objects can be more accurately extracted from a set of the 2D scanning images; and (3) all of the output side of the illumination optical fibers 18, the input side of the imaging optical fiber 28, the two polarizers P1, P2 and the reflection prism 20 are placed and fixed on a metal plate 41 (FIG. 2b) located inside the rectal probe 22 and separated from the cover plastic/glass tube as shown in FIG. 2, so that replacing the disposable plastic/glass cover tube will not change the alignment of the fiber optics. As shown in FIG. 2, the optical fiber-based probe 22 consists of a probe head 22a (intra-cavity section) and a handle section 22b. The probe head 22a has a suitable size to be inserted into a rectum, and the handle section is used for doctors or clinical technicians to hold the probe 22.

Figure 3:
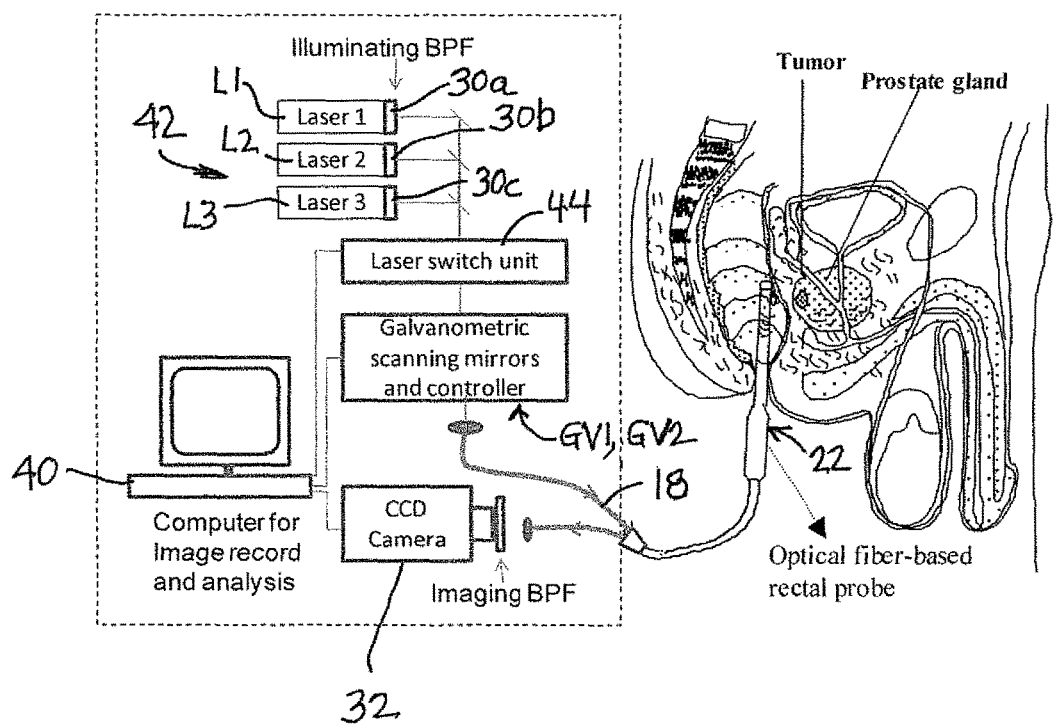
FIG. 3 shows a schematic concept diagram of imaging and detecting prostate cancer through rectum using the NIRPPA, the portable NIR scanning polarization imaging unit with the optical fiber-based rectal probe.

Referring to FIG. 3, the schematic concept diagram of imaging and detecting prostate cancer through rectum using the NIRPPA scanning polarization imaging system. As shown in FIG. 3, the illumination NM light from a laser diodes/LEDs array 42 is selected by a laser/LED switch unit 44. The band pass filters 30a, 30b, 30c in front of the laser diodes L1, L2, L3 are used to ensure the desired illumination wavelength. The selected illumination light is sent to the probe unit 22 after passing through two galvanometric scanning mirrors GV1, GV2 and an illumination fiber bundle 18. The beam then passes through a focus lens 46 and a polarizer P1 (linear or circular polarization element) to generate linear or circular polarization illumination light. The focused polarized illumination light is used to illuminate a prostate through rectum. The two reflecting Galvanometric mirrors GV1, GV2 are used to scan the illumination beam in 2D on the x-y plane of the prostate from point-to-point controlled from the outside of the body. The size of the illumination beam and the imaging area, and the scan steps and speed can be varied.

The NIR light back-scattered from the prostate will first pass through the transparent optical window 22c of the probe head 22, and be reflected from the reflecting prism 20, and is then collected by a lens 26 into a coherent imaging fiber-bundle 28 to form a 2D image of the prostate. Before the light is collected into the coherent imaging fiber-bundle 28, it passes through another linear or circular polarizer P2 placed in front of the detection fiber-bundle 28. This analyzer is kept in the polarization direction, which is perpendicular (or different rotational circular polarization) to that of the illuminating light to reduce the contribution of surface scattering. The image-collecting coherent fiber-bundle is used for transferring images point-by-point, and is coupled into a CCD/CMOS camera 32. For the scattering light imaging, the band pass filter 30 in front of the CCD/CMOS camera is used to pass the scattering light at the desired wavelength and discriminate the fluorescence light emitted from prostate and rectum tissues. Typically, a total number of $n^2$ 2D images will be recorded with an illumination spot scanning by n×n at x-y plane. For example, the total number of 256 2D images will be obtained with a scan of 16×16 points at x-y plane. If the radii of the illumination beam is ~1.5 mm, the separation of two labor illumination spots is 3.0 mm, the scan of 16×16 spots will cover the area of 48 mm×48 mm for the prostate. The better spatial resolution can be obtained with a smaller illumination beam size and a larger number of scan spots.

Figure 4A:
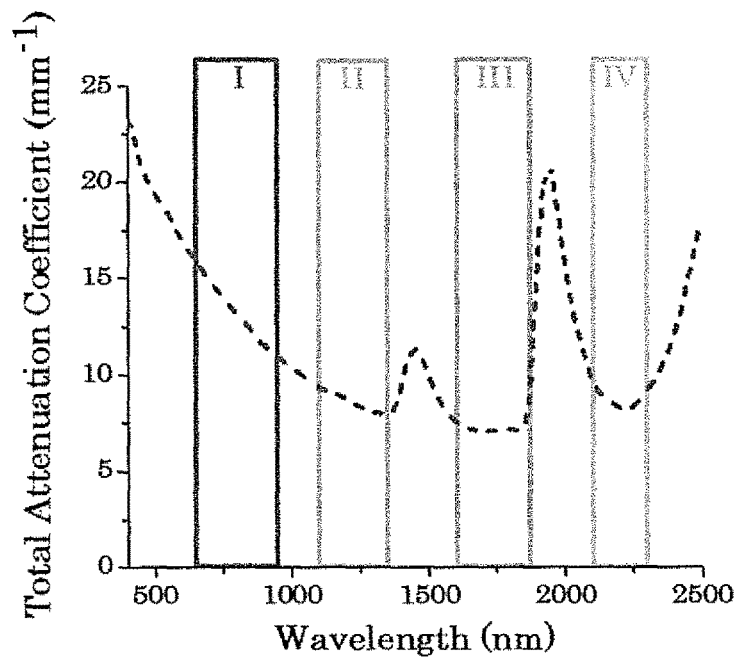
FIG. 4(a) shows the spectrum of the total attenuation coefficient ($\mu_t$) from the normal prostate tissue using #I, #II, #III and #IV NIR tissue optical windows.
Figure 4B:
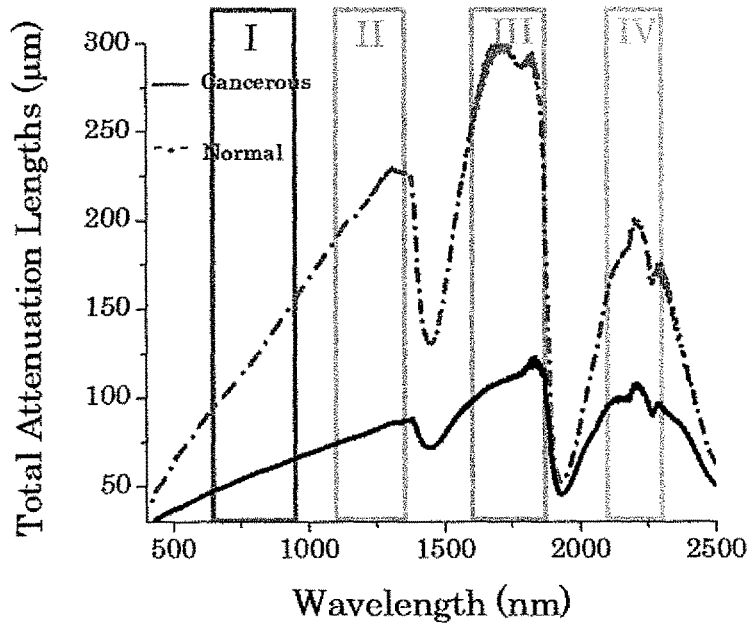
FIG. 4(b) shows the spectra of the total attenuation length ($l_t$) in μm from normal and cancerous prostate tissues using #I, #II, #III, and #IV NIR windows, where $l_t$ is inversely proportional to $\mu_t$.

Referring to FIGS. 4(a) and 4(b), the spectra of the total attenuation coefficient ($\mu_t$) and attenuation length ($l_t$) of the prostate tissues in the four NIR tissue optical windows. The results were obtained from our optical attenuation measurements for thin tissue slices of normal and malignant breast and prostate tissue, pig brain and chicken tissue in the spectral range from 400 nm to 2,500 nm. FIG. 4(a) shows the measured spectrum of the total attenuation coefficient ($\mu_t$) from the normal prostate tissue in #I (650 nm-950 nm), #II (1,100 nm-1,350 nm), #III (1,600 nm-1,870 nm) and #IV (2,100 nm 2,300 nm) NIR tissue optical windows, and FIG. 4(b) shows the spectra of the total attenuation length ($l_t$) in µm from normal and cancerous prostate tissues in the four NIR tissue windows, where $l_t$ is inversely proportional to $\mu_t$. The results indicate that the smaller attenuation coefficient ($\mu_t$) and longer attenuation lengths ($l_t$) can be seen in the second (#II) and third (#III) NIR windows in comparison with the first (#I) window, which may provide additional information to that observed using the conventional first NIR window. The second and third NIR windows may be useful for the deep cancer detection. We also notice that $l_t$ obtained from normal prostate tissue is larger than that from the malignant tissue samples which can be used as a criterion for distinguishing cancerous tissue from their host normal tissue. In order to detect cancerous tissue deeply hidden in organs, the second and third NIR windows should be used, in which the laser diodes/LEDs emitting in the 1,100 nm-1,350 nm and 1,600 nm-1,870 nm spectral ranges should be selected, and the InGaAs-based CMOS NIR camera with a response spectral range of 1,000 nm-1,800 nm, and the InSb-based CMOS NIR camera with a response spectral range of 1,000 nm-5,000 nm should be used.

Figure 5:
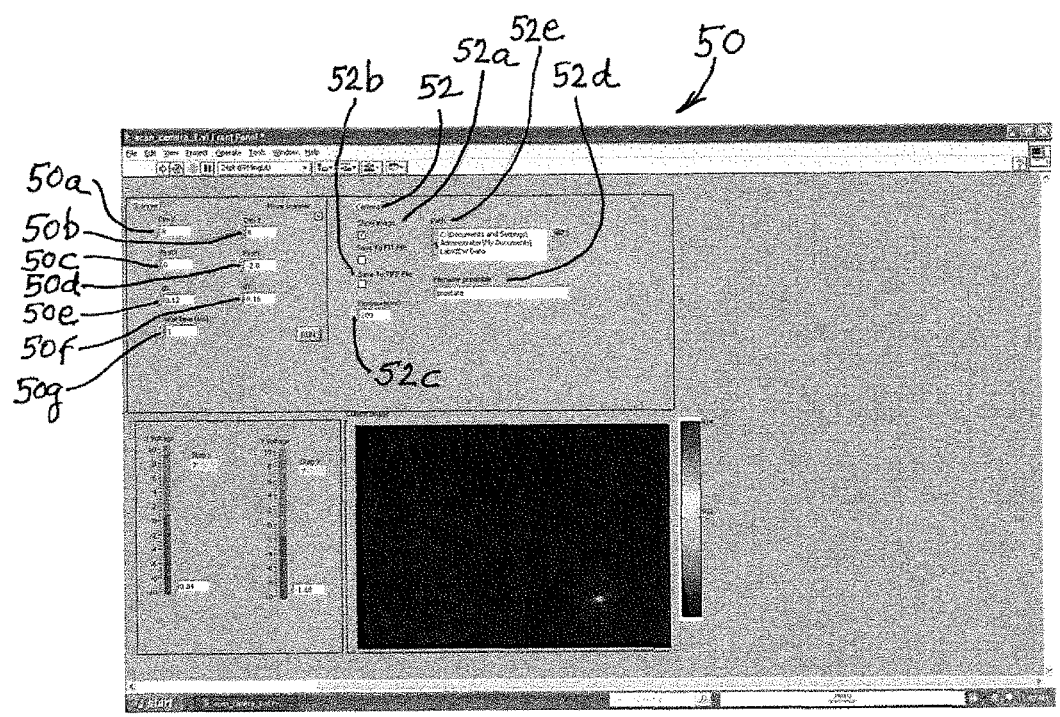
FIG. 5 shows a screenshot of the Graphical User Interface (GUI) after completing an n×n scans. The GUI was developed using the LabVIEW software for operation of the NIRPPA. All operation parameters for the scanning imaging (the original position of the scan, scanning steps, step size, exposure time, and waiting time between two adjacent imaging acquiring, e.g.) can be adjusted through the LabVIEW program.

Referring to FIG. 5, a screenshot 50 of the Graphical User Interface (GUI) is shown after completing an n×n scan. The beam scanning, the image acquiring and recording, and the synchronization of scanning and imaging processes are controlled by the GUI program developed using the LabVIEW software. The functions for controlling the scanning Galvanometric mirrors are indicated at the upper left side shown as "scanner". The buttons 50a, 50b of "Dim X" and "Dim Y" shown in the area of "scanner" are used to control the number of scanning points in the x- and y-directions, respectively. The buttons 50c, 50d of "First X" and "First Y" are used to control the x- and y-positions of the original scanning point (starting point), respectively, and therefore, control the scanning areas on the sample. The buttons 50e, 50f of "dx" and "dy" are used to control the step distance of the x- and y-scanning between two adjacent scanning points, respectively. The button 50g of "wait time (ms)" is used to control the waiting time between two scanning points corresponding to the separate time between two adjacent scanning images, and, therefore, control the scanning speed. The functions for controlling the images' acquiring and recording are indicated at the upper right side shown as "camera" 52. By selecting "Save To FIT File" 52a and/or "Save To TIFF File" 52b, one can activate the function to record the images with the corresponding format. The button 52c of "Exposure" is used to select the camera exposure time in ms. One can change prefix name and path of the image-saving using the function 52d of "Filename preamble" and "path" 52e. In the lower right side, the function of "current image" is used to monitor the real-time recording of the scanning images.

Referring to FIGS. 6(a)-6(d), the graphical illustration for the concept of the OPTICA algorithm. FIG. 6(a) shows the pathway of backscattered light in one direction and the formation of a backscattering image of a host homogeneous medium without inhomogeneous object(s). The image is acquired from photons surviving back from the medium such as normal prostate tissue, which carry the information of optical coefficients of the tissue. FIG. 6(b) exhibits voyage of the backscattered light and their intensity distribution on the source-detector plane in one direction for the host medium with one embedded inhomogeneous object.

The light intensity distribution is contributed by the photons bearing clues about their interacting with the object and the optical coefficients of the tissue. If the difference of the intensity distributions of the images recorded at the two different conditions corresponding to the light propagation shown in FIGS. 6(a) and 6(b) is detectable, ICA can be applied to retrieve the information of the object (IC). More real-world situation (there are multiple inhomogeneous objects in the host medium) is shown by FIG. 6(c), in which the 2D intensity distribution of a backscattering image is mixed by diffused photons with information of the multiple objects. The OPTICA can be used to recover each IC (target) from the mixture perturbation. This will be achieved by using the approach of multiple detectors (CCD/CMOS cameras) and multiple sources (e.g. scanning the illuminated laser beam at different positions on the sample surface in our case) as shown in FIG. 6(d). Each recovered IC mapping to Green's function is used to obtain the 3D image, 3D localization and characterization of the corresponding target by marching the propagation of the scattered light from the target to the surface of the sample until matching the retrieved IC. The OPTICA algorithm has high sensitivity to detect small inhomogeneities with weak contrasts to the host medium because of its capability to separate signal of each IC from huge background noise of the host medium.

Figure 7:
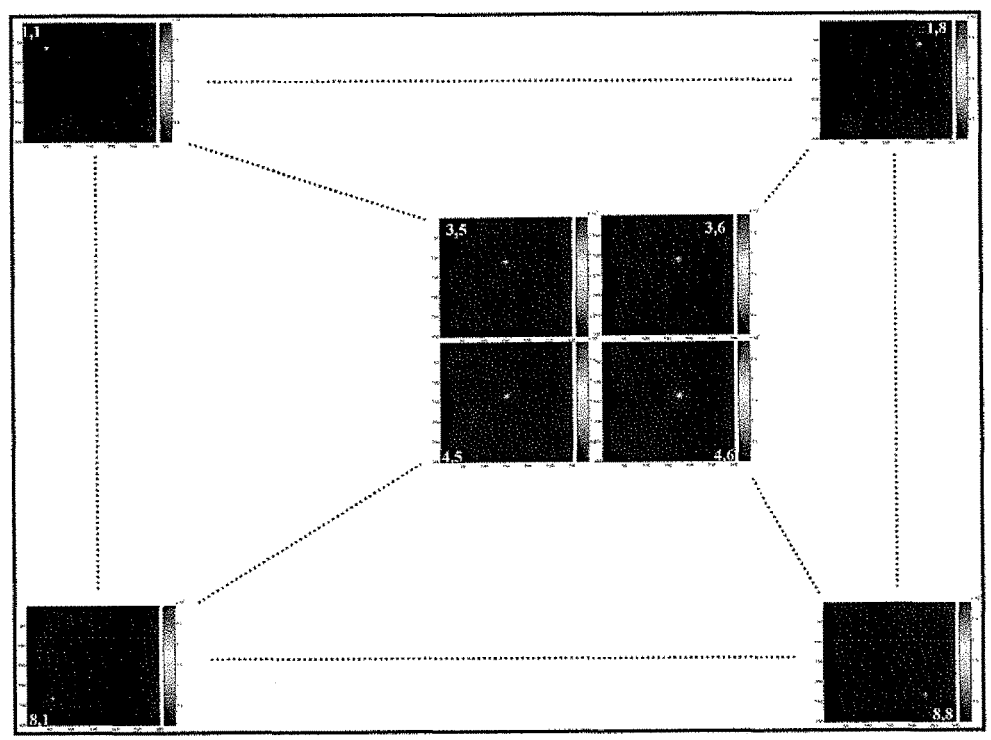
FIG. 7 shows some typical 2D (x-y) images chosen from the total 8×8 2D scanning polarization images recorded by scanning the incident beam on the x-y plane of the prostate tissue sample (a small piece of cancerous prostate tissue hidden in the host normal tissue) with the perpendicular polarization configuration. The images located at the boundary are chosen by the x-y positions of the incident light far from the embedded object while other images at the inside positions are chosen by the x-y position of the incident light close to the embedded cancerous tissue.

Referring to FIG. 7, the typical scanning images of the prostate tissue sample chosen from the total 8×8 scanning polarization images recorded by scanning the incident beam on the x-y plane of the sample. To illustrate the image acquiring procedure and the image analysis using the OPTICA algorithm, a set of scanning polarization images of a prostate tissue sample consisting of a small piece of cancerous prostate tissue embedded in normal prostate tissue were recorded using the NIRPPA system with the backscattering geometry. The images shown on the four corners [images (1, 1), (1, 8), (8, 1), and (8, 8)] are indicated by the x-y positions of the incident light far from the embedded object while other images in the central area [images (3, 5), (3, 6), (4, 5), and (4, 6)] are indicated by the x-y positions of the incident light close to the embedded cancerous tissue. It can be seen that there is no big difference of the light intensity distribution patterns among these recorded images except the position of maximum intensity. This is because of the sharp peak of light intensity scattered from the surface and subsurface in the backscattered direction, which suppresses the perturbation caused by $\delta\mu_a$ and/or $\delta\mu_s$ from the embedded cancerous tissue.

Figure 8:
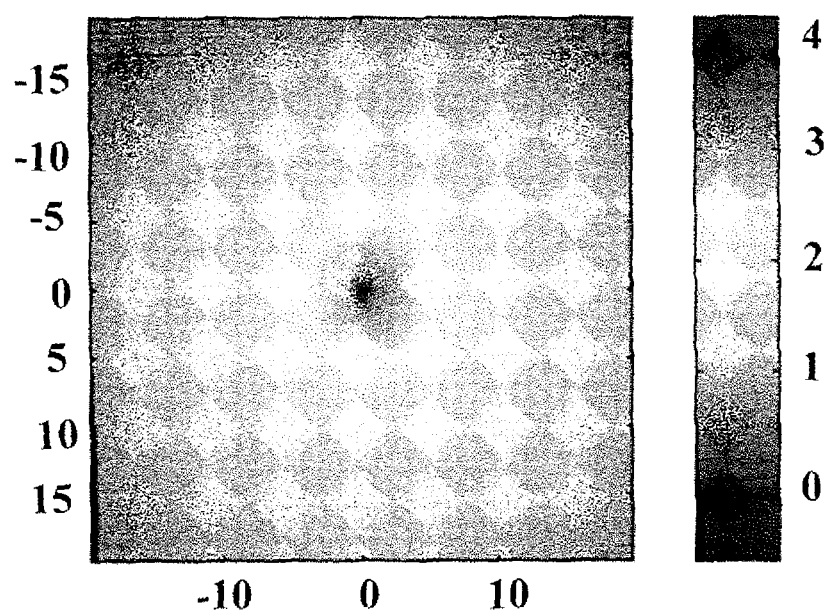
FIG. 8 shows the clean background (host) image shown in a 10-base logarithm scale. In "clean" background image synthesis, the images minimally perturbed by the embedded targets are selected. The "clean" background image is then generated by averaging all selected minimally perturbed images.

Referring to FIG. 8, the "clean" image with 10-base logarithm scale. In the backscattering geometry, a phenomenon of coherent backscattering of light by random media such as human prostate tissue, will generate a peak of scattered light intensity in the backward direction through waves traveling time-reversed paths interfere constructively, which suppresses the perturbation caused by $\delta\mu_a$ and/or $\delta\mu_s$ from the embedded cancerous tissue. A "clean" background image needs to be synthesized to overcome this difficulty. In "clean" background image synthesis, the incident light position of each of 8×8 images is set to origin. All array images are then shifted to the origin and the size of each image is cropped at the boundary while incident light distribution reaches the noise level. The images minimally perturbed by the embedded targets are selected for synthesizing the "clean" image.

Figure 9:
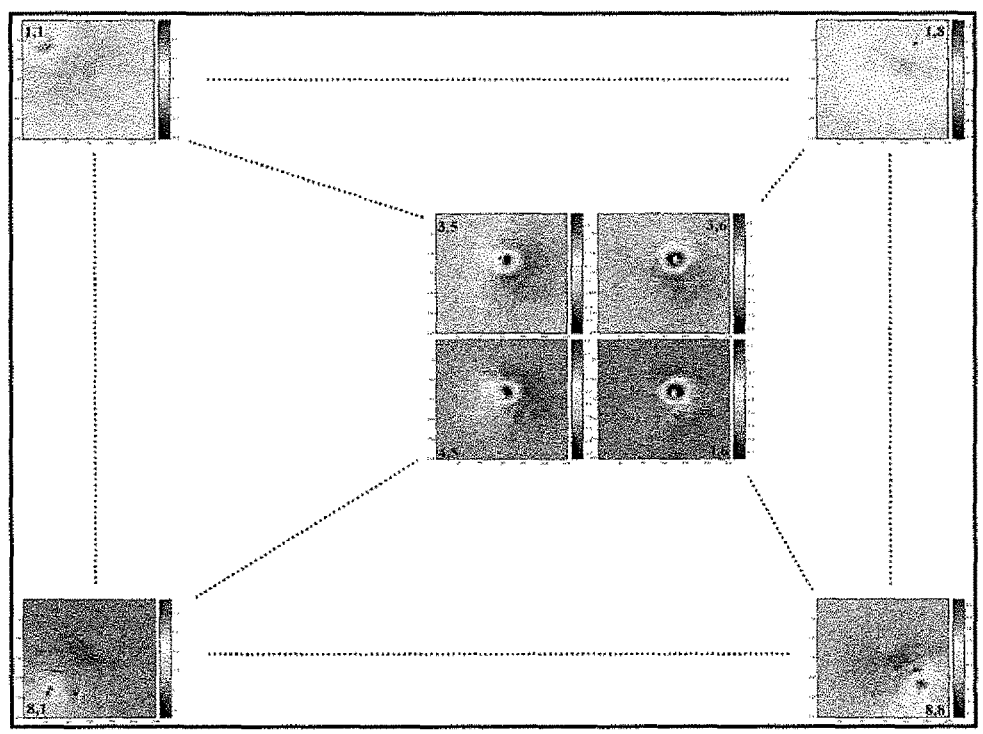
FIG. 9 shows some typical 2D perturbation images generated by extracting the clean image from the recorded images. The 8×8 perturbation images are used to recognize independent components (ICs, i.e. targets), locate their 3D positions and generate 3D image of the prostate sample using the OPTICA algorithm. By subtracting the effect of the coherent backscattering light generated from the surface of prostate tissue sample, the perturbation produced by the embedded cancerous tissue can be obviously observed.

Referring to FIG. 9, the typical perturbation images chosen from the total 8×8 perturbation images. The perturbation 2D (x-y) images are generated by extracting the "clean" background image from the recorded 2D images. The 8×8 perturbation images are used to recognize independent components (targets) and obtain a 3D image of the prostate tissue sample and the 3D positions of the targets using the OPTICA algorithm. By subtracting the effect of backscattering image, the perturbation of the image intensities produced by the embedded cancerous tissue can be obviously observed. One can clearly see from FIG. 9 that the perturbations of images (1,1), (1,8), (8,1), and (8,8) obtained with the incident light at the corner positions of the sample are very small, while the perturbations of images (3,5), (3,6), (4,5), and (4,6) obtained with the incident light at positions between ~row 3 and row 4 and near to column 6 are much distinct. One can estimate that x-y position of the embedded cancerous tissue is around in this area.

Figure 10A:
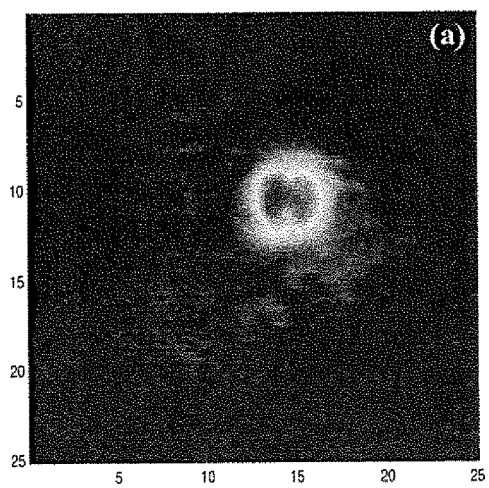
FIGS. 10(a) and 10(b) show the OPTICA-generated intensity distributions contributed from the independent components on the detector plane for the leading IC.
Figure 10B:
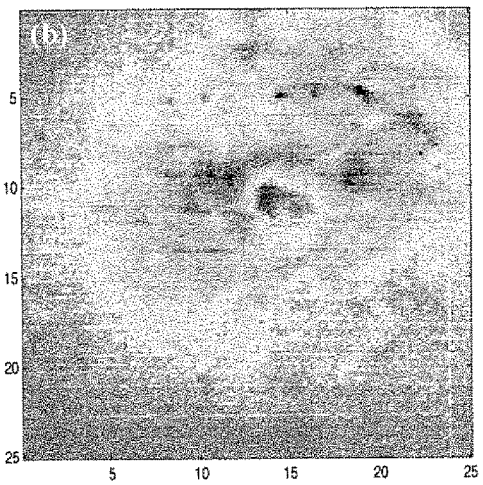
Figure 10C:
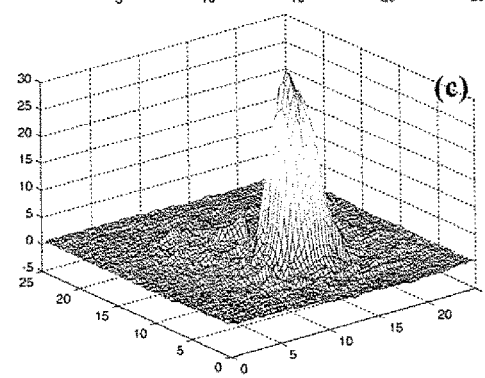
FIGS. 10(c) and 10(d) are for the residual (noise) component. The contribution of each target to the perturbed 2D intensity distribution is obtained by treating each target as an IC. The (x, y)-positions of the target(s) can be obtained using the corresponding IC-perturbed 2D intensity distribution.
Figure 10D:
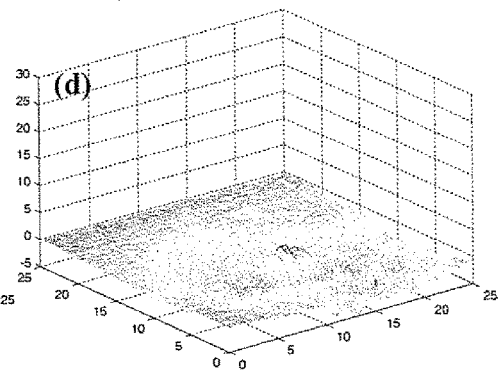

Referring to FIGS. 10(a)-10(d), the OPTICA-generated independent intensity distributions contributed from a cancerous prostate tissue embedded in normal tissue. ICA is performed upon the perturbation images to recognize leading independent components (ICs). The contribution of each target to the perturbed 2D image intensity distribution is obtained by treating each target as an IC. The (x, y)-positions of the target(s) can be obtained using the corresponding IC-perturbed 2D intensity distribution. As an example, FIGS. 10(a) and 10(c) are shown for the leading independent component, and FIGS. 10(b) and 10(d) are for residual (noise) component. It is clear that the existence of the small piece of cancerous prostate tissue can be realized from FIGS. 10(a) and 10(c). The x- and y-locations of the cancer tissue can be obtained from FIG. 10(c). The random intensity distribution of the residual (noise) shown in FIGS. 10(b) and 10(d) indicates the validation of our scanning imaging and the OPTICA approach for the detection of cancerous prostate tissue embedded inside the host normal prostate tissue. Furthermore, the signal strength of FIG. 10(c) is much stronger than that of FIG. 10(d), indicating independent intensity distribution shown in FIG. 10(c) generated by the OPTICA is the leading IC.

Figure 11A:
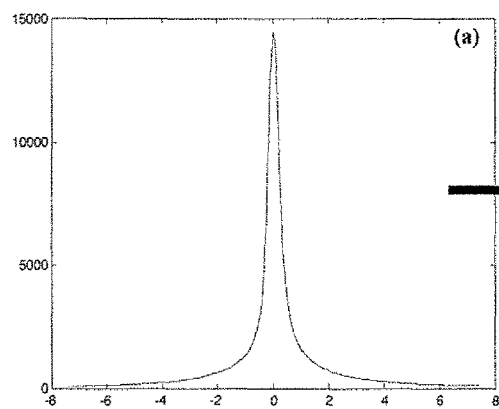
FIG. 11(a) shows the incident light spatial distribution of the clean host medium.
Figure 11B:
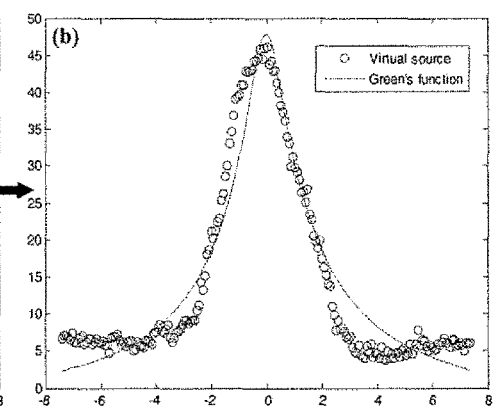
FIG. 11(b) shows the fitting of the Green's function to the independent component along the vertical direction of the sample (z-direction). The OPTICA-generated intensity distributions of the leading independent component(s) on the detector plane can be used to locate the z-position of the cancerous tissue by numerical matching.

Referring to FIGS. 11(a), 11(b) Green's function of the spatial distribution of light intensity without targets obtained from the "clean" image, and the intensity distribution contributed from the leading independent component obtained from the IC-perturbed images, respectively. The OPTICA-generated intensity distributions of the leading independent component on the detector plane can be used to locate the z-position of the cancerous tissue by numerical marching. The z-location of the cancerous prostate tissue (leading IC) can be obtained by fitting Green's function of the target and numerically marching to the surface of the medium obeying diffusion approximation, which yields z=3.1 mm.

Thus, in the NIRPPA system, a NIR beam output from a light source is directed into two galvanometric mirrors to scan the beam in x- and y-directions. The light output from the galvanometric mirrors is then focused into a coherent illumination fiber-bundle using a microscopy objective lens. The output beam from the illumination fiber is directed into a small reflection prism located inside the rectal probe after passing through a polarizer ($P_1$), which is used to ensure that the illumination beam is polarized. The beam reflected from the prism is used to illuminate a prostate through rectum. The light backscattered (or emitted) from the prostate is first passing through the rectal wall and reflected from the same prism inside the probe head. The reflected beam is then collected by a lens into another coherent fiber-bundle used for imaging after passing through another polarizer ($P_2$) working as an analyzer to obtain images with different polarization configurations relative to $P_1$. The image information formed in the imaging fiber-bundle is sent, through a coupling lens, to a CCD/CMOS camera, which can be a Si-based (response for the spectral range of 400 nm-1,000 nm), InGaAs-based (1,000 nm-1,800 nm) or InSb-based (1,000 nm-5,000 nm) camera. Band pass filters are placed in front of the CCD/CMOS camera to record 2D images of the prostate at different wavelengths and depths. The rectal probe of the NIRPPA uses a de-touchable (disposable) transparent plastic/glass tube as a cover tube for the probe head so that in clinical applications, a cover tube can be removed after finishing optical scanning imaging measurements for one patient and a new cover tube can be used for the next patient. Inverse image reconstruction algorithms, such as Optical Tomography using Independent Component Analysis (OPTICA) and others, can be applied to the recorded 2D images to un-mix the signal from cancerous tissue embedded in the host normal tissue in backscattering imaging geometry. The NIRPPA combined with OPTICA was ex-vivo tested to detect cancerous prostate tissue embedded inside large pieces of normal prostate tissue. The results show that NIRPPA can be used to sense weak/small absorptive, scattering or fluorescent inhomogeneities, and may provide an alternative imaging instrument, which is accurate, of high spatial resolution, and less invasive for in-vivo and near-real-time screening and detection of cancers in prostate and other deep organs.

The method bypasses problems in the prior art by using endogenous fluorescent molecules. The use of four NIR spectral windows and configuration of optical components (polarizes, mirrors, lenses, cameras, filters, etc.), is completely unprecedented and produces images of superior quality without injection of potentially toxic substances. The invention has a potential to impact the current techniques for prostate cancer screening and detection.

The innovation of the invention includes: (1) using rectal optical probe to record scanning overlapping images of a prostate through rectum; (2) using ICA and/or other algorithms to produce a 3D image of a prostate and to 3D locate cancerous sites in the early stage of its development; (3) using label-free native fingerprint absorption difference of cancerous and normal prostate tissues for noninvasive detection of the cancerous areas in a prostate without removing prostate tissue and injecting any contrast agents; and (4) detecting and using the sensitive physiological changes such as contents of key biochemical components of prostate tissue for early prostate cancer detection.

The rectal optical probe with galvanometric mirrors that is used to record scanning overlapping images of a prostate has not been reported. A novel algorithm of optical tomography using independent component analysis (OPTICA) and/or other algorithms can be used to obtain 3D image of a prostate from a set of scanned 2D images. The key advantage of the algorithms is their high accuracy of 3D spatial localization of the inhomogeneities and their sensitivity to even weak contrast targets. The nature fingerprint absorption difference of cancerous and normal prostate tissues at the absorption peaks of water, collagen and other key tissue biochemical components will be used to differentiate diseased and healthy prostate tissues, and detect the existence of the cancerous areas within the prostate. These intrinsic absorption properties of tissues can be used as key native spectral markers for prostate cancer detection. In comparison with using extrinsic markers such as contrast agents, the approach according to the invention is natural and safe, providing a noninvasive technique to monitor physiological changes of prostate tissue and detect prostate cancers without removing prostate tissues or injecting contrast agents.

Furthermore, the system uses a removable transparent plastic tube as a cover tube for the optical probe head so that in the clinical applications, a cover tube can be removed after finishing an optical scanning imaging measurement for one patient, and a new cover tube will be used for another patient. With the rectal scanning imaging unit, medical doctors or other medical persons can easily use the unit in the clinical by turning on the switch for the unit, inserting the rectal probe into rectum to image prostate gland through the rectum, operating the rectal probe with the hand-held part, likely they use a rectal probe of an ultrasound system, and remove the used plastic cover tube and place a new cover tube for a new patient. Using disposable plastic cover tubes, patients will be more efficiently protected to do the optical rectal scanning imaging tests.

The application of the invention will impact the current techniques for prostate cancer screening and detection because it may (1) result in a noninvasive optical imaging technique for detecting and 3D-locating cancerous sites in prostate, (2) introduce a new criteria/indicator for prostate cancer screening in addition to the conventional PSA, DRE and TRUS examinations, and (3) enhance the accuracy of diagnosing prostate cancers.

The application of the invention will result in (1) a noninvasive rectal optical imaging approach for obtaining a 3D image of an entire prostate gland, and 3D locations of the cancerous sites in the prostate, and (2) a better guide for the biopsy process. A 3D image of the prostate obtained from the rectal optical imaging and inverse image reconstruction technique can be used to better guide medical personnel to select well-defined areas for biopsy with less sampling and avoid damages of prostate. The invention application may also introduce and advance a new criteria/indicator for prostate cancer screening and detection in addition to the conventional PSA, DRE and TRUS, which would potentially change the clinical management for the prostate cancer screening and detection. In addition, other potential advantages for the invented rectal optical imaging technique include safety, low cost, and user friendliness. The low cost of the rectal NIR scanning polarization imaging unit enables it to be widely used in both doctors' offices and hospitals for screening, making it potential to have significant marketing size.

In the not too distant future, focal therapy (rather than total prostatectomy) will be a treatment option and appropriate imaging will be critical. The pre-operative assessments which can be obtained from the invented approach may demonstrate the potential of the rectum optical imaging for accurate determination of cancer location in prostate for focal therapy. If cancerous sites can be better located, the treatment (either radiation or surgery) can be more appropriately tailored to the individual patient.

The following are aspects of the invention:

(1) Detection Depth. Our preliminary results show that a piece of cancerous prostate tissue embedded in normal prostate tissue at the depth of 3.0 mm was observed using our scattering polarization imaging unit with $\lambda=635$ nm. A black rubber target hidden in chicken breast tissue at depth of 6.6 mm was also detected using the same unit and wavelength [4]. It was also shown that OPTICA is able to resolve absorption, scattering and fluorescence inhomogeneities deeply embedded in both tissue phantoms and ex vivo human tissues as thick as 55 mm and with a transport mean free path 0.9 mm [5]. If longer wavelengths in NIR windows are used, the deeper penetration will be achieved because of the less scattering in the NIR regions. The penetration depth of NIR light into prostate is determined by the transport mean free path ($l_t$) and is greater than 10 $l_t$ in the backscattering geometry. The value of $l_t$ has been measured to be about 2.5 mm for normal prostate tissue at 800 nm. If probing with NIR light around the fingerprint absorption wavelengths of water, collagen and other key components in NIR, the corresponding $l_t$ will be even longer, the penetration depth will be deeper ($\geq 10 \, l_t$, i.e. $\geq 2.5$ cm), and the full prostate may be accessed by NIR light;

(2) Spatial Resolution. The NIRPPA system uses two coherent optical fiber bundles for illumination and imaging. The diameter of a single fiber in the bundles is ~3.2 μm each with numerical aperture N.A.≅0.4. The image information formed in the optical fiber bundle was sent to a CCD camera through the coherent imaging fiber bundle and coupling lens for recording 2D images of the prostate sample. The coupling loss of the system is ~10% and the transverse resolution is 100 μm associated with Air Force resolution target bar chart (AFBC) at group 3. It is known that since ultrasound (TRUS) imaging has poor contrast of cancerous and normal prostate tissues, and poor mm spatial resolution, the TRUS imaging is no longer considered as a first screening and diagnosis test for prostate cancer [6], but it just plays a role in mapping the locations of the biopsy sampling. In contrast, the spatial resolution of the invented scanning imaging is at least one order of magnitude higher than TRUS imaging, and can be used as one of the diagnosis methods;

(3) Dual Scattering and Emission Imagings. In the NIR-PPA system, band pass filters are placed in front of the CCD camera to record the required images with different detecting wavelengths. For the backscattering light imaging, a narrow band filter corresponding to the illumination wavelength is used in front of the CCD camera to ensure that the recorded images are formed only by the light backscattered from the prostate sample. For the tissue emission and/or contrast agent emission light imaging, a long pass filter is used in front of the CCD camera to ensure that the recorded images are formed only by the light emitted from the prostate. As a result, the system can be used, as you respected, with FL markers attached to the specific markers of the prostate tissue.

(4) Detecting Aggressiveness of Prostate Cancer. Relative contents of biochemical components and structure of prostate tissue change with the aggressive level of cancer. Lower Gleason grades are associated with small and closely packed glands. Cells spread out and lose collagen and glandular architecture as Gleason grade increases. Cancers with a high Gleason grades and scores are more aggressive and have a worse prognosis [7,8]. Change of tissue components and structures during cancer development is reflected in their various spectra and images.

In order to detect aggressiveness of prostate cancer using NIRPPA, the following pre-clinical research should be performed to establish the criteria: (1) Perform in-vivo rectal NIR scanning imaging measurements on patients with different grades and stages of prostate cancers before the prostate biopsy, and record sets of 2D images of prostate at the selected wavelengths through rectum; (2) Apply the inverse imaging reconstruction algorithm to detect the existence and 3D locations of cancerous regions in the prostate, and evaluate changes of relative contents and structures and predict the aggressive levels of the cancerous tissue; (3) Perform regular biopsy measurements on the same group of patients; (4) Compare the scanning optical imaging results with the biopsy results and statistically evaluate the positive predictive value of the rectal NIR scanning imaging, i.e. the ratio of the number of each Gleason grade cancerous tissue predicted by the rectal scanning imaging over the number of the corresponding Gleason grade cancerous tissue detected by the conventional biopsy; and (5) Based on the evaluation of the positive predictive value, and the comparison of rectal NIR scanning and ultrasound images, the basic role of the rectal NIR scanning imaging for screening of prostate cancer and prediction of their aggressive levels will be evaluated. In particular, the potential advantages of the rectal NIR scanning imaging-guided biopsy in comparison with the trans-rectal ultrasound-guided biopsy will be investigated. After the criteria are established, the NIRPPA imaging can be used to detect the aggressive level of the prostate cancer.

While the invention has been described in detail and with reference to specific examples and the embodiments thereof, it will be apparent to one skilled in the art that various changes and modifications can be made therein without departing from the spirit and scope thereof.

REFERENCES

[1] Laura A. Sordillo, Yang Pu, Sebastiao Pratavieira, Yury Budansky, and Robert R. Alfano, "Deep optical imaging of tissue using the second and third near-infrared spectral windows", submitted to Journal of Biomedical Optics for publication.

[2] Robert R. Alfano, Jamal H. Ali, Wubao Wang, and Manuel Zevallos, "Detecting human cancer through spectral optical imaging using water absorption wavelengths", U.S. Pat. No. 7,706,862 B2, Date issued: Apr. 27, 2010

[3] Robert R. Alfano, Min Xu, Mohammed Alrubaiee, and Swapan Kumar Gayen, "Optical tomography using independent component analysis for detection and localization of targets in turbid media", U.S. Pat. No. 7,826,878, Date Issued: Nov. 2, 2010.

[4] Y. Pu, W. B. Wang, M. Xu, G. C. Tang, Y. Budansky, M Sharanov, S. Achilefu, J. A. Eastham and R. R. Alfano, "Near infrared photonic finger imager for prostate cancer screening", Technol. Cancer Res. Treat. (Technology of Cancer Research and Treatment), 10, Issue 6, 507-517 (2011).

[5] M. Xu, M. Alrubaiee, S K. Gayen and R. R. Alfano (2005). "Three-dimensional localization and optical imaging of objects in turbid media using independent component analysis," *Appl. Opt.* 44: 1889-1897, 2005.

[6] Ferrini, R., and Woolf, S. H., "Screening for Prostate Cancer in American Men", http://www.acpm.org/prostate.htm, *American College of Preventive Medicine—Practice Policy Statement.*

[7] Gleason, D. F., (1977), "The Veteran's Administration Cooperative Urologic Research Group: histologic grading and clinical staging of prostatic carcinoma", In Tannenbaum, M. *Urologic Pathology: The Prostate*, Philadelphia: Lea and Febiger, pp. 171-198. ISBN 0-8121-0546-X.

[8] Epstein, J. I., Allsbrook, W. C. Jr, Amin, M. B., and Egevad, L. L.; ISUP Grading Committee, (2005), The 2005 International Society of Urological Pathology (ISUP) Consensus Conference on Gleason. Grading of Prostatic Carcinoma, Am. J. Surg. Pathol;

What is claimed:

1. An infrared (IR) Photonic Analyzer System comprises an IR Scanning polarization unit for generating an illumination beam and receiving an image beam;

an elongate generally cylindrical optical probe dimensioned and configured for insertion into a rectum, said optical probe defining an optical path and having a transparent optical window for transmitting an illumination beam towards a tissue of an internal organ and for receiving the image beam from the internal organ;

an illumination optical fiber transmitting said illumination beam along said optical path from said IR scanning polarization unit to said optical probe;

an image optical fiber transmitting said image beam along said optical path from said optical probe to said IR scanning polarization unit;

a first polarizer within said optical probe between said illumination optical fiber and said transparent optical window for polarizing said illumination beam with a first polarization prior to transmission along said optical path onto the internal organ;

a second polarizer within said optical probe between said transparent optical window and said image optical fiber for polarizing with a second polarization said image beam received from the internal organ along said optical path prior to transmission to said image optical fiber, said first and second polarizations being perpendicular to each other to reduce front surface scattering and increase depth of imaging, said IR scanning polarization unit using said illumination beam having a wavelength anywhere within at least one of the following IR tissue optical windows: Window #1 (650 nm-950 nm); Window #2 (1,100 nm-1,350 nm); Window #3 (1,600 nm-1,870 nn) and Window #4 (2,100 nm-2300 nm), said first and second polarizers being arranged to prevent transmission of said illumination beam with said first polarization from entering said image optical fiber while enabling transmission of said image beam with said second polarization into said image optical fiber;

and means for establishing and comparing the total attenuation lengths of said image beam for non-cancerous and cancerous tissues and determining that the tissue is likely to be cancerous when its total attenuation length is equal to or less than 50% of the attenuation length of non-cancerous tissue in a corresponding one of said at least one of said IR tissue optical windows.

2. The system of claim 1, wherein the system uses a wavelength anywhere within the following IR tissue optical windows for imaging: Window # II (1,100 nm-1,350 nm) and Window #III (1,600 nm-1,870 nm) and Window #IV (2,100 nm-2,300 nm).

3. The system mentioned in claim 1, further comprising means for performing image analysis by Optical Tomography using Independent Component Analysis (OPTICA) to characterize and obtain 3D images and locations of cancerous tissue embedded in healthy, non-cancerous tissue in backscattered geometry.

4. The system of claim 3, further comprising CCD/CMOS cameras used as multiple channel detectors to record IR images in said IR tissue optical windows, said CCD/CMOS cameras having at least one of Si sensors responsive to the spectral range of 400 nm-1,000 nm, InGaAs sensors responsive to the spectral range of 1,000 nm-1,800 nm, and InSb-based (1,000 nm-5,000 nm) cameras having a dynamic range of 16 or over, which can obtain enough dynamic range of intensity distribution for the OPTICA analysis monitoring for cancer.

5. The system of claim 1, further comprising: (1) optical components (band pass filters, polarizers, and lenses), a detector (CCD/CMOS cameras), dual axis galvanometric mirrors, (2) two servo driver circuit boards, and (3) a drive unit for sending voltage output to servo circuit boards, to acquire multiple source, multiple detector signal for an OPTICA analysis to detect abnormal tissue inside internal organs.

6. The system of claim 1, wherein the system comprises lasers diodes/light emission diodes (LEDs) with built-in or external modulation, the emission wavelengths of said laser diodes/LEDs being in the spectral ranges of said NIR tissue optical windows.

7. The system of claim 1, further comprising a reflection prism within said optical probe arranged to illuminate the tissue of the internal organ.

8. The system of claim 1, wherein light backscattered from tissue of the internal organ is collected by said image optical fiber coupled with a charge-coupled device/complementary metal-oxide semiconductor ("CCD/CMOS") camera.

9. The system of claim 1, wherein said illumination beam is modulated with said first polarizer and said image beam is modulated with said second polarizer with a perpendicular configuration to cancel coherent backscattering (CBS).

10. The system of claim 1, further comprising a Graphical User Interface (GUI) software is used to control a number of scanning points in the x- and y-directions, a scanning step size, and a camera's exposure time.

11. The system of claim 1, further comprising a CCD/CMOS imaging system with coherence imaging fibers.

12. The system of claim 1, further comprising a transparent tube dimensioned to removably receive said optical probe.

13. A method of establishing when a tissue is cancerous comprising the steps of generating an infrared (IR) illumination beam and receiving an image beam by an elongate generally cylindrical optical probe dimensioned and configured for insertion into a rectum;

transmitting the illumination beam through a transparent optical window of said optical probe at tissue of an internal organ and for receiving the image beam from the internal organ;

transmitting said illumination beam through an illumination optical fiber along an optical path to said optical probe;

transmitting said image beam through an image optical fiber along said optical path from said optical probe;

polarizing said illumination beam in said optical probe between said illumination optical fiber and said transparent optical window for polarizing with a first polarization prior to transmission along said optical path onto the organ tissue;

polarizing said image beam received from the organ tissue along said optical path within said optical probe between said transparent optical window and said image optical fiber for polarizing with a second polarization prior to transmission to said image optical fiber, said first and second polarizations being perpendicular to each other to reduce front surface scattering and increase depth of imaging, said illumination beam having a wavelength anywhere within at least one of the following IR tissue optical windows: Window #1 (650 nm-950 nm); Window #2 (1,100 nm-1,350 nm); Window #3 (1,600 nm-1,870 nm) and Window #4 (2,100 nm-2300 nm), said first and second polarizations being selected to prevent transmission of said illumination beam with said first polarization from entering said image optical fiber while enabling transmission of said image beam with said second polarization into said image optical fiber;

and establishing and comparing the total attenuation lengths of said image beam for non-cancerous and cancerous tissues and determining that the tissue is likely to be cancerous when its total attenuation length is equal to or less than 50% of the total attenuation length of normal non-cancerous tissue in a corresponding one of said at least one of said IR tissue optical Windows.

14. A method as defined in claim 13, wherein said determination is made in more than one of said at least one of said IR tissue optical Windows.

15. A method as defined in claim 13, where said total attenuation length of the cancerous tissue is within the range of 35 and 50 percent of the total attenuation length of non-cancerous tissue.

16. A method of establishing when a tissue is cancerous comprising the steps of generating an infrared (IR) illumination beam and receiving an image beam by an elongate generally cylindrical optical probe dimensioned and configured for insertion into a rectum;

transmitting the illumination beam through a transparent optical window of said optical probe at tissue of an internal organ when inserted into a rectum and receiving the image beam from the internal organ;

transmitting said illumination beam through an illumination optical fiber along an optical path to said optical probe;

transmitting said image beam through an image optical fiber along said optical path from said optical probe;

polarizing said illumination beam in said optical probe between said illumination optical fiber and said transparent optical window for polarizing with a first polarization prior to transmission along said optical path onto the internal organ;

polarizing said image beam received from the internal organ along said optical path within said optical probe between said transparent optical window and said image optical fiber for polarizing with a second polarization prior to transmission to said image optical fiber, said first and second polarizations being perpendicular to each other to reduce front surface scattering and increase depth of imaging, said illumination beam having a wavelength anywhere within at least one of the following IR tissue optical windows: Window #1 (650 nm-950 nm); Window #2 (1,100 nm-1,350 nm); Window #3 (1,600 nm-1,870 nm) and Window #4 (2,100 nm-2300 nm), said first and second polarizations being selected to prevent transmission of said illumination beam with said first polarization from entering said image optical fiber while enabling transmission of said image beam with said second polarization into said image optical fiber;

and establishing and comparing the total attenuation lengths of image beams for the tissue in at least two of said Windows and determining that the tissue is likely to be cancerous when its peak total attenuation length in at least one of said two Windows has a predetermined relationship to the peak total attenuation length in the other of said Windows.

17. A method as defined in claim 16, wherein said predetermined relationship is that the peak total attenuation length in Window 2 is less than the peak total attenuation length in Window 4.

* * * * *